United States Patent [19]
Opitz

[11] Patent Number: 5,932,238
[45] Date of Patent: Aug. 3, 1999

[54] GALANTHAMINE CONTAINING TRANSDERMAL APPLICATOR FOR THE TREATMENT OF ALCOHOLISM

[75] Inventor: K. Opitz, Münster, Germany

[73] Assignees: LTS Lohmann Therapie-Systeme GmbH & Co., Neuwied; KG and Hefa-Frenon Arzneimittel GmbH & Co. KG., Werne, both of Germany

[21] Appl. No.: 07/953,439

[22] Filed: Sep. 29, 1992

Related U.S. Application Data

[63] Continuation of application No. 07/675,835, Mar. 27, 1991, abandoned.

[30] Foreign Application Priority Data

Mar. 29, 1990 [DE] Germany .............................. 40 100 79

[51] Int. Cl.$^6$ .............................. A61K 9/70; A61K 31/55
[52] U.S. Cl. ........................... 424/448; 424/449; 514/215
[58] Field of Search ............................ 514/215; 424/448, 424/449

[56] References Cited

U.S. PATENT DOCUMENTS

| | | | |
|---|---|---|---|
| 4,663,318 | 5/1987 | Davis ....................................... | 514/252 |
| 4,761,429 | 8/1988 | Blum et al. . | |
| 4,777,173 | 10/1988 | Shrotryia et al. ........................ | 514/561 |
| 5,089,267 | 2/1992 | Hille et al. .............................. | 424/449 |

FOREIGN PATENT DOCUMENTS 3843239 2/1990 Germany .

OTHER PUBLICATIONS

Haboubi, N.A. et al, Ann. Clin. Biochem. 23(4); 458–62 1986.
Hsu, L.L. et al., Alcohol Clin Exp Res 7(3); 249–55 1983.
Stojek, A et al., BR J Addict 82(8); 927–30; 1907.
Daunderer, M., Fortschr Med 101 (17); 778–80 1983.
Power, J.S. et al.; J.Clin. Pharmacol. 21(1); 57–60 1981.
Riley, E.P. et al., Alcohol Clin Exp Res 10(1); 50–53 1986.
Paskov, D.S.: "Galanthamine." in: New Neuromuscular Blocking Agents, 31:653–72 Springer–Verlag Berlin, Heidelberg, New York, Tokyo (Ed.) (1986).
Snorrason, E., Stefansson, J.G.: "Galanthamine hydrobromide in mania." Lancet, 337: 557 (1991).
Stojek, A., Napierala, K.: "Physostigmine in eyedrops decreases craving for alcohol in early withdrawal treated with carbamazepine." Materia Medica Polona, 4: 249–54 (1986).
Tanahashi, T., Poulev, a., Zenk, M.H.: "Radioimmunoassay for the quantitative determination of Galanthamine." Planta Medica, 56: 77–81 (1990).
Tencheva, J., Yamboliev, I., Zhivkova, Z.: "Reversed–phase liquid chromatography for the determination of galanthamine and its metabolites in human plasma and urine." Journal of Chromatography, 421: 396–400 (1987).

Thomsen, T., Bickel, U., Fischer, J.P., Kewitz, H.: "Stereoselectivity of cholinesterase inhibition by galanthamine and tolerance in humans." Eur. J. Clin. Pharmacol., 39: 603–5 (1990).
Thomsen, T., Zendeh, B., Fischer, J.P., Kewitz, H.: "In vitro effects of various cholinesterase inhibitors on acetyl– and butyrylcholinesterase of healthy volunteers." Biochemical Pharmacology, 41: 139–41 (1991).
Thomsen, T., Kaden, B., Fischer, J.P., Bickel, U., Barz, H., Gusztony, G., Cervos–Navarro, J., Kewitz, H.: "Inhibition of Acetylcholinesterase activity in human brain tissue and erythrocytes by Galanthamine, Physostigmine and Tacrine." Eur. J. Clin. Chem., Clin. Biochem. 29: 487–92 (1991).
Thomsen, T., Kewitz, H.: "Selective inhibition of human acetylcholinesterase by Galanthamine in vitro and in vivo." Life Sciences, 46: 1553–58 (1990).
Vlahov, R., Krikorian, D., Spassov, G., Chinova, M., Vlahov, I., Parushev, S., Snatzke, G., Ernst, L., Kieslich, K., Abraham, W.–R., Sheldrick, W.S.: "Synthesis of Galanthamine and related alkaloids—New approaches." Tetrahedron, 45: 3329–45 (1989).
J. Ruprecht et al: "The involvement of the central cholinergic and endorphinergic systems in the nitrous oxide withdrawl syndrome in mice." Anesthesiology, V. 58, No. 6, 1983, pp. 524–526.
Bickel, U., Thomsen, T., Weber, W., Fischer, J.P., Bachus, R., Nitz, M., Kewitz, H.: "Pharmacokinetics of galanthamine in humans and corresponding cholinesterase inhibition." Clin. Pharmacol. Ther., 50: 420–28 (1991).
Cozanitis, D.A., Toivakka, E.: "Treatment of respiratory depression with the anticholinesterase drug galanthamine hydrobromide." Aneasthesia, 29: 581–84 (1974).
Cozanitis, D.A.: "Galanthamine hydrobromide, a longer acting anticholinesterase drug, in the treatment of the central effects of Scopolamine (Hyoscine)." Anaesthesist, 26: 649–50 (1977).
Cozanitis, D.A., van de Pol, F., van Wezel, H., Crul, J.F.: "Antagonistic activity of galanthamine on constant infusion of pancuronium in rats." Experientia, 37: 1326–27 (1981).
Cozanitis, D.A., Friedmann, T., Fürst, S.: "Study of the analgesic effects of Galanthamine, a Cholinesterase Inhibitor." Archives Inter. de Pharmacodynamie et de Teérapie, 266: 229–38 (1983).
Foitzik, H., Lawin, P.: "Klinische Erfahrungen mit Galanthamin (Nivalin) als Antidot von Pancuronium." Z. prakt. Anästh., 7:203–7 (1972).

(List continued on next page.)

*Primary Examiner*—Marianne M. Cintins
*Assistant Examiner*—M. Moezie
*Attorney, Agent, or Firm*—Sprung Kramer Schaefer & Briscoe

[57] ABSTRACT

Galanthamine and the pharmaceutically suitable acid addition salts thereof can be used for the treatment of alcoholism; these compounds are released from adequate pharmaceutic formulations which are administered, e.g., orally, transdermally, or otherwise parenterally, in a continuous and controlled manner.

4 Claims, No Drawings

OTHER PUBLICATIONS

Göpel, W., Bertram, W.: "Erfahrung mit Nivalin in der neurologischen Therapie." Psychiat. Neurol. med. Psychol., 23: 712–18 (1971).

Mayrhofer, O.: "Erfahrungen mit Galanthamin (Nivalin) als Antagonist der Relaxantien vom Curaretyp." Bull. schweiz. Akad. med. Wiss., 23: 48–52 (1967).

Mihailova, D., Yamboliev, I., Zhivkova, Z., Tencheva, J., Jovovich, V.: "Pharmacokinetics of Galanthamine Hydrobromide after single subcutaneous and oral dosage in humans." Pharmacology, 39: 50–58 (1989).

Naranjo, C.A., Sellers, E.M. (Ed.): "Drug treatments for alcoholism: The need for innovation." "Drug treatments for alcoholsm: The need for innovation." in: Research Advances in New Psychopharm. Treatments for Alcoholism, 1–9 Elsevier Science Publishers B.V. (1985).

Baraka, A., Harik, S.: "Reversal of central anticholinergic syndrome by Galanthamine." JAMA, 238: 2293–94 (1977).

Bastida, J., Viladomat, F., Llabrés, J.M., Quiroga, S., Codina, C., Rubiralta, M.: "Narcissus nivalis: A new source of Galanthamine." Planta Medica, 56: 123–24 (1990).

GALANTHAMINE CONTAINING TRANSDERMAL APPLICATOR FOR THE TREATMENT OF ALCOHOLISM

This is a continuation of application Ser. No. 07/675,835, filed Mar. 27, 1991, now abandoned.

DESCRIPTION

The present invention relates to the use of galanthamine as well as the pharmaceutically suitable acid addition salts thereof for the treatment of alcoholism. These compounds are released in a continuous and controlled manner from adequate pharmaceutical formulations which are administered, e.g., orally, transdermally or otherwise parenterally.

The present invention in particular provides pharmaceutical formulations which release suitable compounds in a controlled manner to treat alcoholism.

Whereas today the acute withdrawal and the treatment of the perilous alcoholic delirium in special wards do not constitute medical problems, there is still no satisfying treatment of chronic alcoholism. About 80% of the treated alcoholics get a relapse within the term of one year. They are in need of a remedy against the alcohol desire resulting in the relapse, which remedy is reliably effective and well tolerated.

Although chronic alcoholism involves many human problems and severe damage with respect to the national economy, the innovation of the drug therapy for chronic alcoholism is stagnating all over the world (Naranjo, C. A., Sellers, E. M., Excerpta medica, Amsterdam—New York—Oxford, 1–9, (1985) and this in particular applies to the Federal Republic of Germany (Rommelspacher, H., Wanke, K., Caspari, D., Topel, H., Dtsch. Arzteblatt 86, 2197-B2204 (1989).

The drugs used to control the influence of alcohol and the alcoholism must be divided into:
1. sobering agents (amethystics),
2. remedies to treat the potentially fatal alcohol poisoning, e.g., naloxone (Narcanti®), physostigmine,
3. palliatives for the acute alcohol withdrawal, e.g., neuroleptics (Neurocil®, Melleril®), piracetam, clonidine, carbamazepine, and for the alcoholic delirium: clomethiazole (Distraneurin®),
4. substances blocking the alcohol catabolism at the acetaldehyde stage thus creating an artificial alcohol intolerance.

Disulfiram (Antabus®)—the main representative of this group—is the most frequently used drug for the treatment of alcoholism. However, Antabus® is no therapeutic substance, since the ingredients and substances related thereto neither reduce the strong desire for alcohol nor influence the cause of the disease (Heinz, G., Therapie-Handbuch, Alkoholismus, 2nd ed., Urban & Schwarzenberg, München-Wien-Baltimore, 1257–1258 (1987):
5. Agents alleviating the compulsive desire for alcohol (the so-called "craving") and thus are supposed to prevent treated alcoholics from relapsing. There is an urgent need in particular for these drugs. However, an effective drug for the treatment of the chronic alcoholism has not been found until today.

Clinical tests using fenfluramine and bromocriptine have not been repeated and verified (Krasner, N., Moore, M. R., Goldberg, A., Booth, K. D., Frame, A.H., Mc Laren, A. D., Brit. J. Psychiat. 128, 346–353 (1976), Borg, V., Acta psychat. scand. 68, 100–110 (1983).

The hopes held out with respect to the lithium therapy of the chronic alcoholism have not come true (Gallant, D. M., Clin. Exp. Res. 9, 297–298 (1985), Dorus, W., Ostrow, D. G., Anton, R., Cushman, P., Collins, T. F., Schäfer, M. Charles, H. L. Desai, P., Hayashida, M., Malkerneker, U., Willenbring, M., Fiscella, R., Sather, M. R., J. Amer. med. Assoc. 262, 1664–1652 (1989), Naranjo, C. A., Sellers, E. M., Roack, C. A., Woodley, D. V., Sandoz-Craig, M., Sykora, K., Clin. Pharmacol. Ther. 35, 374–381 (1984).

The best results were achieved with zimelidine, however, this serotonin-resumption-inhibitor, which was on the market as antidepressant under the Tradename Normud®, had to be withdrawn due to severe side effects and thus is not available any longer.

It is thus the object of the present invention to provide a drug which—by the controlled release from an oral, transdermal, or otherwise parenteral formulation—permits an effective and practical treatment of alcoholism by reducing the desire for alcohol.

This object is achieved according to the invention by a formulation and the use thereof for the treatment of alcoholism, which is characterized in that it contains an effective amount of the active substance galanthamine (4a, 5, 9, 10, 11, 12-hexahydro-3-methoxy-11 -methyl-6H-benzofuro [3a, 3, 2-ef] [2] benzazepine-6-ol)

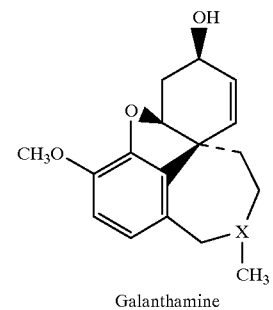
Galanthamine or one of the pharmaceutically acceptable acid addition salts thereof.

This solution is surprising all the more since the pharmacologic effects of galanthamine were examined thoroughly, but the effect, namely that of reducing the alcoholic's desire for alcohol, which is due to galanthamine in a galanthamine-containing formulation has not been described until today.

The extraction of galanthamine is carried out by isolation from the Caucasian snowdrop Galanthus woronowii Vel., Amaryllidaceae (Proskurnina, Y., J. Gen. Chem. 22, 1899 (1952) or by synthesis (Kametani, T. et al, J. Chem. Soc. C., 6, 1043–1047 (1971), Shimizu, K. et al, Heterocycles 8, 277–282 (1977).

Due to its pharmacological properties galanthamine belongs to the group of the reveribly acting cholinesterase inhibitors. The effects of galanthamine are similar to those of physostigmine and neostigmine, however, it has additional special effects. The therapeutic range of galanthamine is 3 to 6 times larger than that of physostigmine or neostigmine, because of its lower toxicity (Paskov, D. S., ed. Springer-Verlag, Berlin—Heidelberg—New York—Tokyo, 653–672 (1986).

This advantage compensates its slightly lower dose-related cholinesterase inhibition.

Galanthamine is used in anesthesiology to abolish muscle relaxation after the administration of depolarizing muscle relaxants (Mayrhofer, O., Bull. schweiz. Akad. med. Wiss. 23, 48–52 (1967).

In contrast to neostigmine, galanthamine overcomes the blood-brain barrier and opposes the cerebral effect of cholinergic poisons. Galanthamine has the effect of awakening the patient from the twilight sleep caused by scopolamine (Baraka, A., Harek, S., J. Amer. Med. Assoc. 238, 2293–2294 (1977).

Due to the long duration of action, galanthamine, which incorporates the properties of physostigmine and neostigmine, is a valuable agent in anesthesiology, since many patients suffer from a central anticholinergic syndrome after a general anaesthesia (Cozanitis, D. A., Anaesthesist 26, 649–650 (1977).

In addition to the cholinergic effects, galanthamine considerably influences the respiratory center. Due to the abolishment of respiratory depressions caused by morphine derivatives, galanthamine is a useful antidote in the neuroleptic analgesia (Foitzik, H., Lawin, P., Z. prkt. Anästh. 7, 203–207 (1972), Cozanitis, D. A., Toivakka, E., J. Amer. Med. Assoc. 240, 108 (1978).

Galanthamine is used in neurology for the treatment of paresis of the facial nerves and other mono- and polyneuropathies, residual paraplegia after poliomyelitis or brain and/or spinal cord injuries, as well as in case of myasthenia gravis. In case of myasthenia galanthamine-hydrobromide (Nivalin®) is said to have a longer duration of effect than neostigmine (Prostigmin®) (Göpel, N., Bertram, N., Psychiat., Neurol. med. Psychol. 23, 712–718 (1971).

In the ophthalmology galanthamine serves for the symptomatical treatment of the narrow-angle glaucoma (Catalino, P. U., Bolletino d'oculesta 42, 100–119 (1963), Leydhecker, W., Glaukom. Ein Handbuch, 2nd ed., Springer-Verlag, Berlin—Heidelberg—New York, 531 (1973).

The use of galanthamine is tested in the treatment of the Alzheimer's disease (Domino, E. F., Current Research in Alzheimer Therapy, Galanthamine. Another look at an old cholinesterase erihibitory E. Giacobini, R. Becker, eds. Saylor & Francies, New York—Philadelphia—Washington DC—London, 295–303 (1988).

The present invention is directed to formulations through which galanthamine or one of the pharmaceutically acceptable acid addition salts therof is released in a continuous and controlled manner.

Forms of administration releasing active substances in a controlled manner are known in the state of the art. The administration of pharmaceutically effective compounds by means of such formulations can be effected orally, transdermally or otherwise parenterally.

Suitable formulations for the oral administration within the scope of the present invention will be described in the following.

In such a formulation, the pharmaceutic active substance is encapsulated in a semi-permeable membrane, e.g., made of cellulose acetate. By means of a drill or laser a tiny hole is drilled into the material of the capsule. Within the body of the treated patient water is absorbed through the material of the capsule. The pharmaceutic active substance is slowly forced in the desired constant and controlled manner through the tiny opening by osmotic pressure. Such systems are described in U.S. Pat. Nos. 3,760,805, 3,760,806, 3,764,984, 3,845,770, 3,916,899, and 3,987,790. The pharmaceutic active substances may be present in such systems in solid form or absorbed to ion-exchange resins.

Another system for the oral administration according to the present invention is described by Sheth and Leeson in U.S. Pat. No. 4,137,300. This patent describes a formulation containing a wax matrix.

The active substances of the present invention are administered by corresponding formulations in an adequate and suitable manner. Solid active substances may be administered in solution or as dispersion. The solution or dispersion medium may be inorganic or organic. Suitable solution or suspension media for galanthamine are, e.g., water, silicone oil, or mineral oil.

By silicone oils linear polymeric dimethyl siloxanes are to be understood, and by mineral oils the distillation products obtained from mineral raw materials (petroleum, lignite and coal tar, wood, peat), which distillation products mainly consist of mixtures of saturated hydrocarbons.

To permit the administration of a formulation as described above, the following additives may be added to the system:

antioxidants, synergists, stabilizers, preservatives, taste corrigents, coloring agents, solvents, solutizers, surfactants (emulsifiers, solubilizers, wetters, defoamers), agents influencing viscosity and consistency, gel formers, absorption accelerators, adsorbents, moisturizers, lubricants (e.g., flow regulating agents), agents influencing disintegration and dissolution, fillers (extenders), peptisers;

release retarders.

This list is not to be understood as being complete. many substances perform more than one function so that they are to be assigned to several of the stated auxiliary agent groups. Some kinds of starch are, for example, used as fillers in the production of tablets and powders. They are, however, at the same time flow regulating agents, adsorbents, hydrogel formers, and viscosity increasers.

Suitable physiologically acceptable substances are known to the skilled artisan.

In a formulation for the transdermal administration of compounds according to the present invention, the pharmaceutical active substance may be contained in a matrix from which it is released in the desired gradual, constant, and controlled manner. The permeability of the matrix when the compound is released is based on diffusion. Such a system is described in the German Patent 33 15 272. This system consists of an impermeable covering layer, a supersaturated active substance reservoir of an polymeric matrix which is connected to said covering layer and is of special construction, a pressure-sensitive-adhesive layer connected to the reservoir and being permeable to the active substance, and a protective layer covering the pressure-sensitive-adhesive layer which is removable prior to use. It is also possible to use systems the reservoir layer of which is of such a self-adhesiveness that it also represents the pressure-sensitive-adhesive layer.

When the active substance is absorbed through the skin, the person to be treated in this way receives a controlled and predeterminable amount of active substance.

Further suitable formulations are described in U.S. Pat. Nos. 3,742,951, 3,797,494, 3,996,934, and 4,031,894. These formulations basically consist of a backing representing one of the surfaces, an adhesive layer being permeable to the active substance and representing the other surface, and, finally, a reservoir containing the active substance between the two layers forming the surfaces. As an alternative, the active substance may be contained in a plurality of microcapsules which are distributed within the permeable adhesive layer. In each case the active substance is released continuously from the reservoir or the microcapsules through a membrane into the adhesive layer which is permeable to the active substance and in contact with the patient's skin or mucosa. Where microcapsules are used, the material of the capsules may act as membrane.

Suitable formulations for an otherwise parenteral application of galanthamine and the salts thereof are those which permit a depot effect of the active substance. In this connection, the formulation is applied as an injectable solution on non-aqueous base. Suitable solvents are known to the skilled artisan. Examples are vegetable oils prescribed by some pharmacopeias.

Main representatives of this group are peanut oil, olive oil, almond oil, sunflower oil, soy bean oil, and sesame oil. Castor oil frequently exhibits a particularly favorable solubility for drugs; in addition oils of animal origin are suitable too. The oils are physiologically indifferent and well tolerated. It is essential in this connection that these oils are especially purified and exhibit low acid- and peroxide-values. Since an intravenous application is not possible because of lack of miscibility with the blood serum and probable pulmonary embolism, they can only be used for intramuscular and subcutaneous injection preparations. Oily solutions and suspensions remain at the place of application for a rather long period of time (frequently for up to one month) and release the active substances in a protracted manner.

The dosage level of galanthamine and the pharmaceutically acceptable salts thereof must be high enough to achieve an enduring action; it has to be adjusted individually.

The active substance content of the present formulation preferably is between 0.1 to 90%-wt, particularly preferred between 5 and 20%-wt, relative to the total weight of the formulation.

The invention will be illustrated by the following example:

EXAMPLE

Influence of galanthamine-hydrobromide on the voluntary alcohol consumption of rats which genetically prefer ethanol.

As test animals 6 female rats of a phylon originating from the Finnish AA-rat-line were used in each case.

The animals of this inbred strain prefer to drink 10% alcohol if they have the -free choice between the alcohol and pure water.

The animals were separately kept in macrolon cages type 3 at 23° C. room temperature, the air was changed nine times per hour. Only during the dark hours from eight p.m. to eight a.m. they were provided with unlimited amounts of granular dry feed (Altromin 1311; flour to which vitamins, mineral substances, amino acids, and trace elements are added; manufacturer: Altromin Spezialfutterwerke GmbH [works manufacturing special food for animals], of 4937 Lage (Lippe), FRG), drinking water, and ethanol solution (10% v/v.); in this connection special vessels were used ensuring feeding and drinking without loss. The amounts consumed were determined by gravimetry; the consumed amounts of liquid were determined automatically and continuously by means of twelve weighing cells. The criterion for the alcohol preference was the respective proportion of ethanol solution of the total amount stated in terms of percent: 0% means that only water and no ethanol solution was drunk, 100% means that only ethanol solution was consumed. The average preference for alcohol of the untreated test animals was 78% and 83%, respectively.

The results are stated in the following table:

TABLE

The influence of galanthamine-hydrobromide on the ingestion behavior of female ethanol-preferring rats (n = 6). The values established during the respective three-day preliminary period without administration of galanthamine are given in the round brackets.

| Dosage [mg/kg oral] | 5 | 10 |
|---|---|---|
| Weight, KG [g] | 215 ± 6.2 | 213 ± 4.9 |
| Preference for alcohol[%] | (82.8 ± 6.4) | (77.8 ± 4.3) |
| | 45.0 ± 12.9** | 51.7 ± 6.4*** |
| Alcohol consumption | (6.47 ± 0.43) | (6.30 ± 0.34) |
| absolute [g/kg/KG] | 3.17 ± 0.89** | 3.71 ± 0.42*** |
| Total amount drunk | (97.2 ± 2.3) | (100.9 ± 1.9) |
| [g/kg KG] | 89.8 ± 5.6 is | 90.6 ± 6.1 is |
| Food intake | (55.2 ± 1.3) | (55.7 ± 2.1) |
| [g/kg KG] | 57.7 ± 2.6 is | 44.6 ± 7.6 is |

Student's t-test (K. Stange, Angewandte Statistik, Springer-Verlag Berlin/Heidelberg 1970) for paired values
** p 0.01
*** p 0.001
is = insignificant It can be taken from the table that the administration of galanthamine considerably reduces the desire for alcohol.

Food intake and total drinking amount are only insignificantly influenced.

It is understood that the specification and examples are illustrative but not limitative of the present invention and that other embodiments within the spirit and scope of the invention Will suggest themselves to those skilled in the art.

I claim:

1. A transdermal applicator comprising
   a) an impermeable backing layer,
   b) a polymer matrix connected to said backing layer and containing as active substance galanthamine (4a, 5, 9, 10, 11, 12-hexahydro-3-methoxy-11-methyl-6H-benzofuro [3a, 3, 2-ef] [2] benzazepine-6-ol), and
   c) a pressure-sensitive adhesive element for fixing the applicator to the skin.

2. The transdermal applicator according to claim 1, which also contains a membrane controlling the release of the active substance.

3. The transdermal applicator according to claim 1, which also contains a removable protective layer.

4. The transdermal applicator according to claim 2, which also contains a removable protective layer.

* * * * *